United States Patent
Dorr et al.

(10) Patent No.: US 7,314,300 B1
(45) Date of Patent: Jan. 1, 2008

(54) FIBER OPTIC SURGICAL HEADLIGHT SYSTEM

(75) Inventors: Justin Dorr, Cherry Valley, MA (US); Johannes M. Blum, Jacksonville, FL (US); James D. Hunter, Hilliard, FL (US)

(73) Assignee: Sunoptic Technologies LLC, Jacksonville, FL (US)

( * ) Notice: Subject to any disclaimer, the term of this patent is extended or adjusted under 35 U.S.C. 154(b) by 248 days.

(21) Appl. No.: 11/119,400

(22) Filed: Apr. 29, 2005

(51) Int. Cl.
G02B 6/32 (2006.01)
G02B 6/42 (2006.01)
F21V 14/06 (2006.01)
F21V 21/084 (2006.01)
A61B 1/07 (2006.01)

(52) U.S. Cl. ............ 362/581; 362/105; 362/277; 362/319; 362/570; 362/572

(58) Field of Classification Search ............ 362/581, 362/105, 106, 570, 572, 804; 600/249; 385/90, 385/119
See application file for complete search history.

(56) References Cited

U.S. PATENT DOCUMENTS

| | | | |
|---|---|---|---|
| 3,285,242 A | 11/1966 | Wallace | 600/249 |
| 3,745,993 A | 7/1973 | Feinbloom | 600/249 |
| 3,830,230 A | 8/1974 | Chester | 600/249 |
| 3,951,139 A | 4/1976 | Kloots | 600/249 |
| 4,104,709 A | 8/1978 | Kloots | 362/105 |
| 4,290,422 A | 9/1981 | Burton | 600/249 |
| 4,516,190 A | 5/1985 | Kloots | 362/370 |
| 4,616,257 A | 10/1986 | Kloots et al. | 348/370 |
| 4,797,736 A | 1/1989 | Kloots et al. | 348/370 |
| 5,268,977 A | 12/1993 | Miller | 385/33 |
| 5,430,620 A | 7/1995 | Li et al. | 362/572 |
| 5,709,459 A | 1/1998 | Gourgouliatos et al. | 362/105 |
| 5,769,523 A | 6/1998 | Feinbloom | 362/554 |
| 5,774,271 A | 6/1998 | Lagerway et al. | 359/649 |
| 6,120,161 A | 9/2000 | Van Der Bel | 362/105 |
| 6,224,227 B1 | 5/2001 | Klootz | 362/105 |
| 6,523,984 B2 * | 2/2003 | Belfer | 362/581 |

FOREIGN PATENT DOCUMENTS

| | | | | |
|---|---|---|---|---|
| JP | 60052816 A | * | 3/1985 | 385/119 |
| JP | 62014614 A | * | 1/1987 | 385/119 |

* cited by examiner

*Primary Examiner*—Alan Cariaso
(74) *Attorney, Agent, or Firm*—Howson & Howson LLP

(57) ABSTRACT

A kit, or family, of interchangeable headlamp parts for a headlight system is provided that enables illuminated light spots of different sizes and/or different light distribution styles to be produced. The headlight system includes a headband, a headlamp mounted on the headband, a light source, and a fiber optic cable having one end connected to the light source and an opposite end tip connected to the headlamp. According to one embodiment, an upper assembly of the headlamp includes a cable mounting module that is moveable relative to a core module and that permits the distance between the end tip of the fiber optic cable and a convergent lens to be adjusted to permit spots with different light distributions to be produced. A method of adjusting the light projected by a headlight system is also provided.

19 Claims, 4 Drawing Sheets

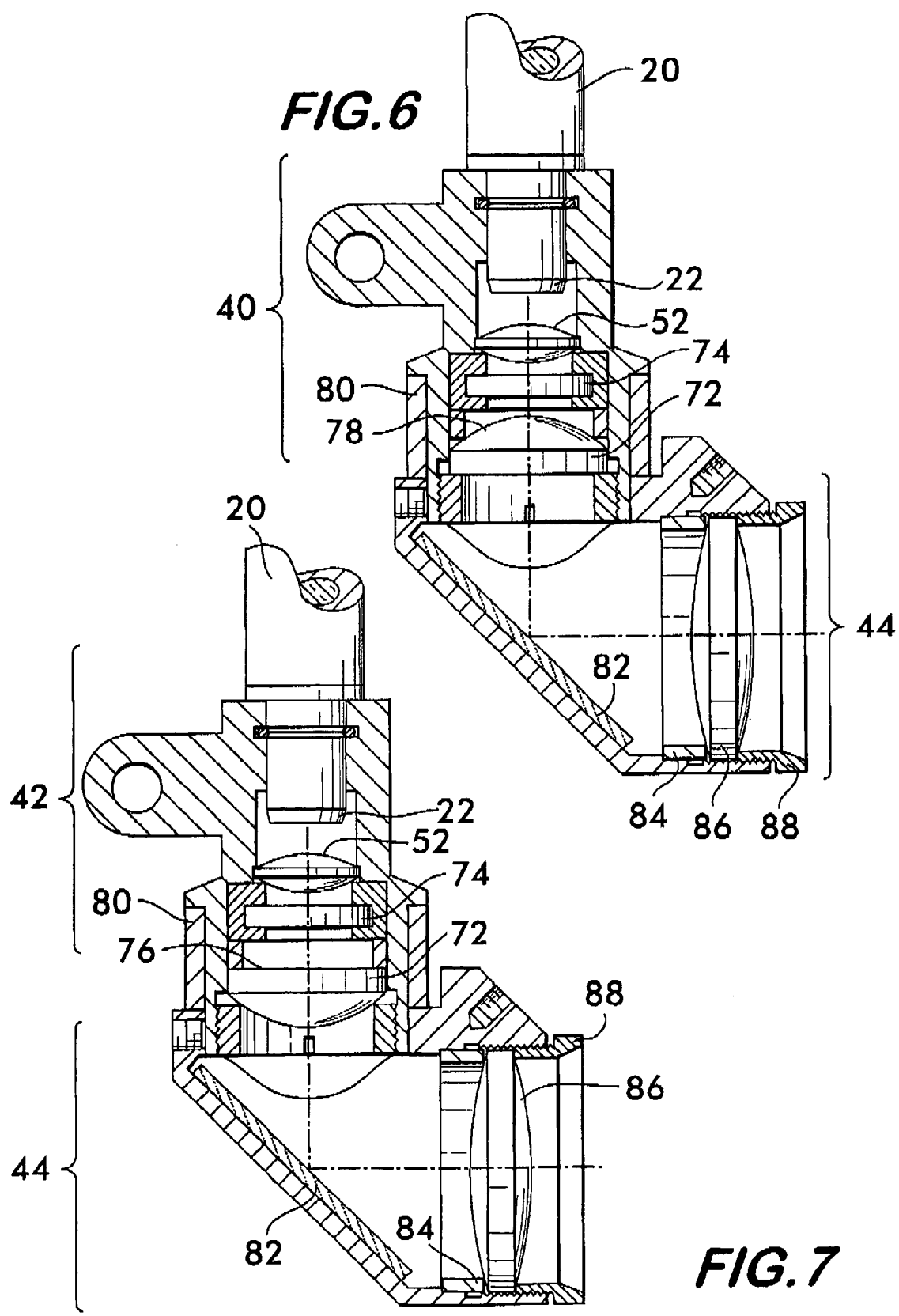

FIBER OPTIC SURGICAL HEADLIGHT SYSTEM

BACKGROUND OF THE INVENTION

Fiber optic headlights are worn on the head of surgeons, technicians, and like individuals for directing a spotlight beam of intense light coincident with the wearer's line of sight, independent from overhead and/or ambient lighting. The headlights include a headlamp that receives an emitting end of a fiber optic cable and that focuses and directs the light from the cable into a beam aimed forward of the wearer. The headlamp includes an assembly of optic elements that is preferably configured in a tubular elbow which depends from a headset, or headband, at the wearer's forehead to a location approximately between the wearer's eyes.

A typical headlamp receives a male end tip of the fiber optic cable in a port having a captive, spring-wire snap-ring that engages a circumferential groove on the end tip and thereby holds the end tip in a fixed position relative to the optics in the headlamp. The divergent light emitted by the end tip is directed through a convergent lens, or lens system, and iris diaphragm (if so equipped) to a mirror where it is reflected forward through a final lens. The visual characteristics of the light beam projected by the headlamp are determined by the entire train of components from the initial light source to the emitting lens of the headlamp. Typically, the only controls with respect to the projected light are brightness, which is effected by a moveable shutter incorporated in the light source cabinet, and the size of the spot of light on a surface at a predetermined distance from the headlamp, which is effected by adjusting the iris orifice (if so equipped) within the headlamp.

If the optical system of the headlight is perfectly focused, the projected beam carries an undesirable image of the assembled fibers at the emitting surface of the end tip thereby producing a dense honeycomb of shadows between the individual fibers. The projected beam will also carry an undesirable image of any small particles of dust which may be present on any of the optics. To alleviate these problems, the optic system is intentionally slightly defocused to blend such images away from visibility. However, this is a sensitive technique, since defocusing also causes undesirable rings and haloes of light and shadows to appear in the projected beam and spot of light, and the overall brightness of the beam and spot of light diminishes.

Different models of headlights produce different spot diameters and different distributions of light within the spot. Typically, two styles of light distribution are utilized. One is a sharply defined spot having even brightness throughout. The other is a less sharply defined spot having intense brightness in the interior of the spot fading off toward the peripheral outer edges of the spot. Both styles are functions of the degree to which the optic system is defocused. Users of headlights have personal preferences which may depend upon particular operating conditions.

Examples of headlight systems are provided by U.S. Pat. Nos. 5,430,620 issued to Li et al.; 3,285,242 issued to Wallace; 5,709,459 issued to Gourgouliatos; 5,774,271 issued to Lagerway et al.; 6,224,227 issued to Klootz; 6,120,161 issued to Van Der Bel; 5,769,523 and 3,745,993 issued to Feinbloom; 4,616,257 and 4,797,736 issued to Kloots et al.; 4,516,190, 4,104,709 and 3,951,139 issued to Kloots; and 4,290,422 issued to Burton. U.S. Pat. No. 5,268,977 issued to Miller is directed to a fiber optic luminaire.

Although the aforementioned headlights may function in a satisfactory manner for their intended purposes, there is a need for a headlight system that enables ready adjustability of beam quality. For instance, the headlight system preferably should permit the distribution of light within a light beam and spot to be readily altered in a convenient and uncomplicated manner and without having to alter the diameter of the beam or spot. In addition, the headlight system should preferably provide a kit, or family, of different readily interchangeable parts all constructed from similar or the same components to enable the user to produce a desired spot size and/or spot style within a range of choices.

SUMMARY OF THE INVENTION

The present invention is a kit, or family, of interchangeable headlamp parts for a headlight system. The kit includes a plurality of upper assemblies each housing a convergent lens system and having a port for releaseably engaging an end tip of a fiber optic cable. The upper assemblies are made from common parts provided in different arrangements. The kit also includes at least one elbow assembly that houses a mirror and an exit, or emitting, lens and that is releaseably engageable with each of the upper assemblies. Illuminated light spots of different sizes and/or distribution styles are produced depending upon which upper assembly is selected to construct the headlamp.

According to another aspect of the present invention, a headlight system comprises a headband, a headlamp mounted on the headband, a light source, and a fiber optic cable having one end connected to the light source and an opposite end tip connected to the headlamp. The headlamp has an upper assembly and an elbow assembly. The elbow assembly includes a mirror and an exit lens. The upper assembly includes a cable mounting module and a core module. The cable mounting module has a port for releaseably engaging the end tip of the fiber optic cable, and the core module houses at least one convergent lens. The cable mounting module is moveable relative to the core module and permits the distance between the end tip of the fiber optic cable and the convergent lens to be adjusted. This adjustment permits the headlamp to produce a sharply defined spot of light with substantially even brightness throughout as well as a less sharply defined spot of light with intense brightness at a center of the spot fading off toward peripheral edges of the spot.

According to a further aspect of the present invention, a method of adjusting the light projected by a headlamp of a headlight system is provided. The method includes securing a headband of a headlight system to the head of a user and attaching one end of a fiber optic cable to a light source and an opposite end tip to a headlamp mounted on the headband. The headlamp has an upper assembly with a cable mounting module and a core module. The cable mounting module has a port for releaseably engaging the end tip of the fiber optic cable, and the core module houses at least one convergent lens. Preferably, the method includes a step of moving the cable mounting module relative to the core module to adjust a distance between the end tip of the fiber optic cable and the convergent lens. The method can also include the step of interchanging the parts of the headlamp to provide a desired spot size and/or distribution style.

BRIEF DESCRIPTION OF THE DRAWINGS

The foregoing and other objects, features and advantages of the present invention should become apparent from the following description when taken in conjunction with the accompanying drawings, in which:

FIG. 6 is a cross-sectional view of a fourth embodiment of a headlamp assembly according to the present invention; and FIG. 7 is a cross-sectional view of a fifth embodiment of a headlamp assembly according to the present invention.

DETAILED DESCRIPTION OF THE INVENTION

Figure 1:
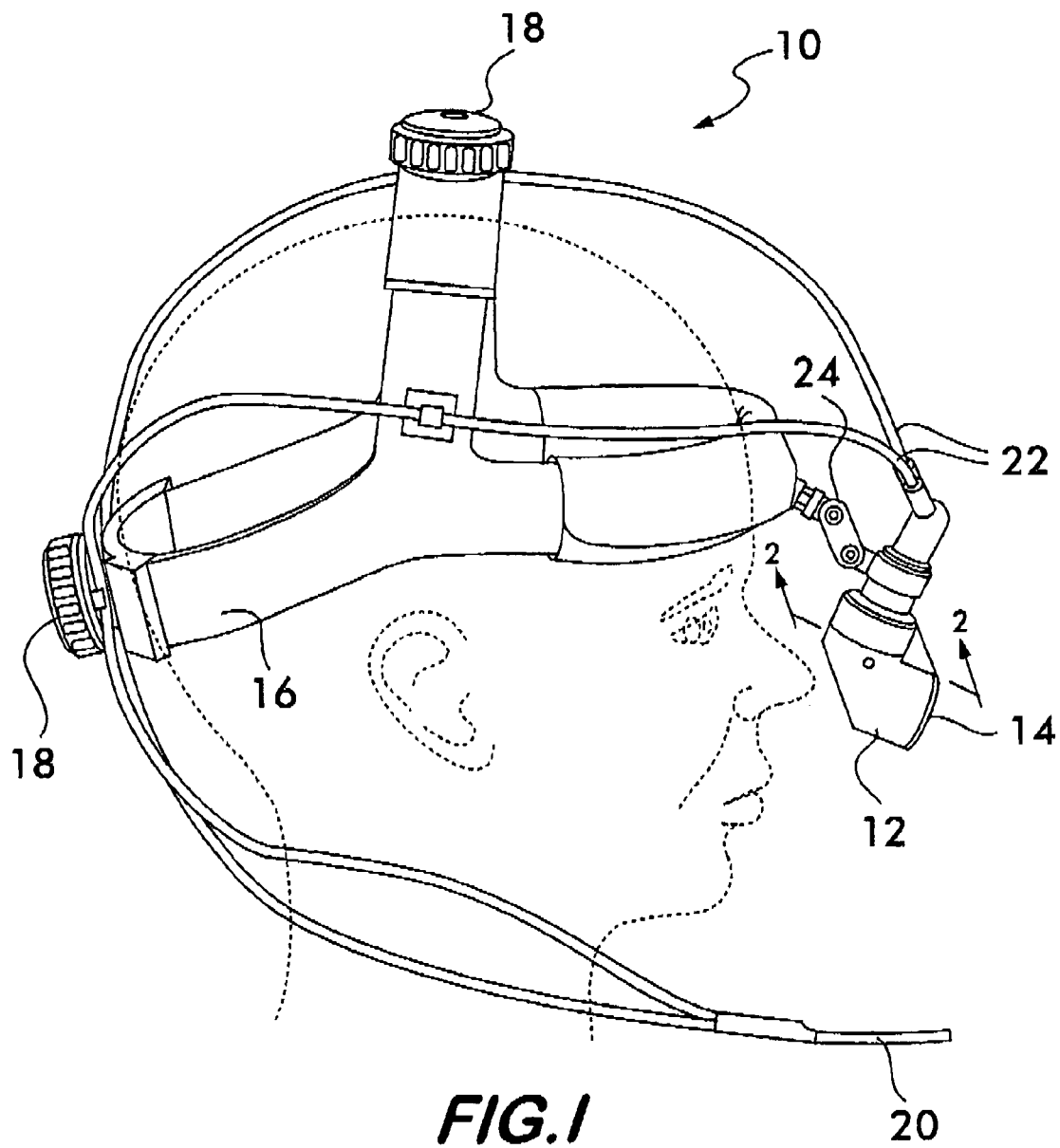
FIG. 1 is a perspective view of a headlight according to the present invention shown mounted on the head of a surgeon or other individual.

The headlight system according to the present invention includes a headset 10 and a light source (not shown). The headset 10 can be worn on a person's head as best illustrated in FIG. 1 to position a hands-free lamp, or headlamp, 12 adjacent the wearer's forehead. Preferably, the headlamp 12 has a light emitting end 14 positionable at a location between the wearer's eyes to project a spotlight beam of intense light coincident with the wearer's line of vision. Such headlights can be worn by surgeons during surgical procedures or by other individuals during other activities that require a spot lighting.

The illustrated headset 10 is provided as a headband 16 with knobs 18 permitting adjustment thereof. Alternatively, the headband 16 can be made of a lightweight, breathable, stretchable fabric material that does not require adjustment knobs. The light source (not shown) can be a box like instrument, such as a xenon light source, that is located on the floor, supported on a nearby table or shelf, or mounted on the belt of the headset wearer. A fiber optic cable 20 has one end (not shown) connected to the light source and an opposite end tip, or end tips, 22 connected to the headlamp 12, which is connected via a linkage 24 to the front of the headband 16. Preferably, the cable 20 runs along the back of the head of the wearer and is connected to the top of the headlamp 12 so that the cable 20 does not obstruct the movement or vision of the headset wearer. See FIG. 1.

FIGS. 2-7 illustrate headlamps 26 (FIGS. 2 and 3), 28 (FIG. 4), 30 (FIG. 5), 32 (FIG. 6) and 34 (FIG. 7) which each include an upper assembly 36, 38, 40 or 42 and an elbow assembly 44 or 46. Preferably, the upper assemblies can be readily mounted to and removable from the elbow assemblies so that a kit, or family, of upper and/or elbow assemblies can be provided to a user so that the user can select between various combinations of assemblies to provide a light beam and spot of desired characteristics. Preferably, each of the upper assemblies is made of similar or the same components, although arranged differently, and each of the elbow assemblies is made of similar or the same components, although arranged differently.

Figure 2:
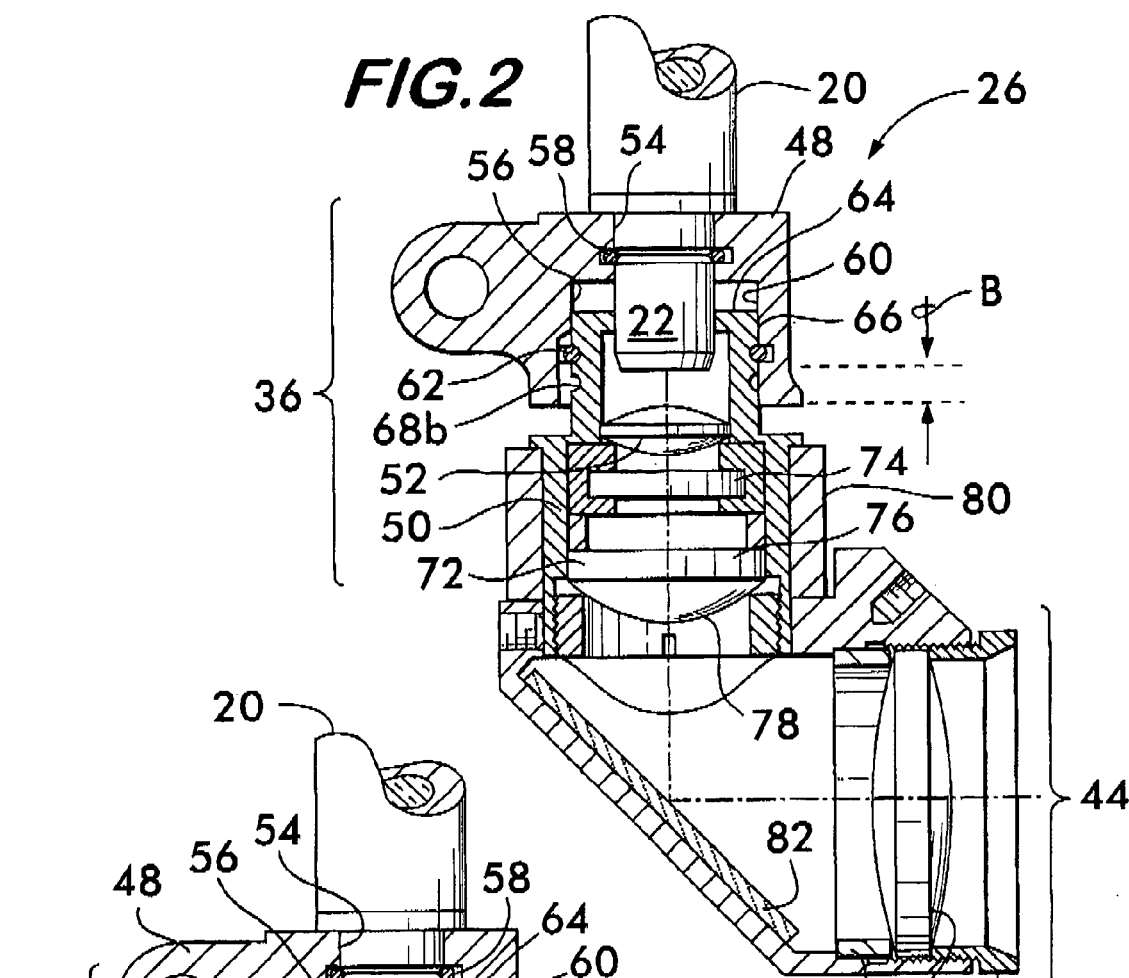
FIG. 2 is a cross-sectional view of a first embodiment of a headlamp assembly according to the present invention.
Figure 3:
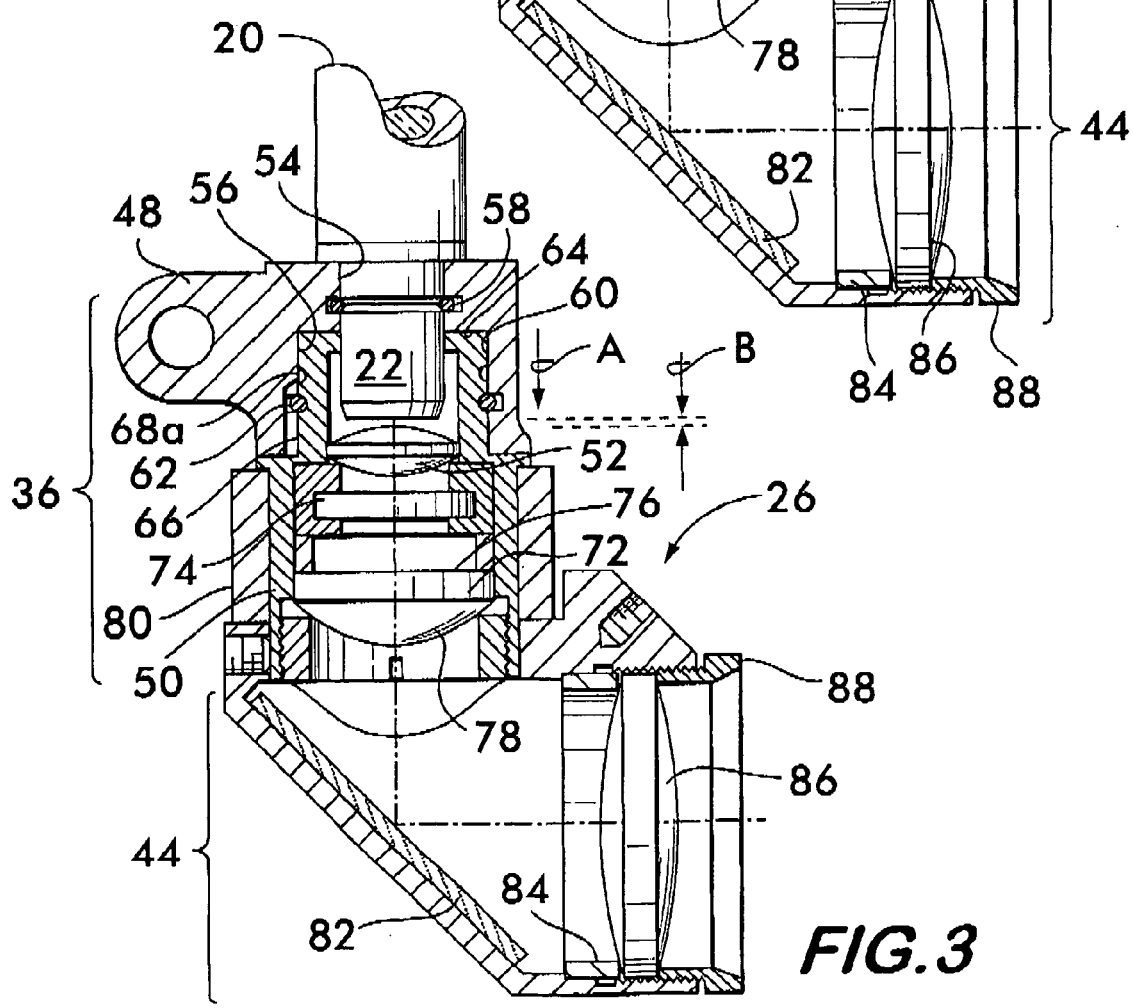
FIG. 3 is a cross-sectional view of the headlamp illustrated in FIG. 2 in which the spaced distance between the end tip of the fiber optic cable and the convergent lens has been reduced.

Turning first to the headlamp 26 illustrated in FIGS. 2 and 3, a headlamp is provided that enables the user to readily produce light beams and spots with different light distributions without altering the diameter of the spot size that is formed on a surface a predetermined distance from the headlamp. For purposes of example, headlamp 26 may be configured to produce a relatively large light spot about 140 mm in diameter on a surface that is spaced about sixteen inches from the emitting end 14 of the headlamp. Due to the construction of the headlamp 26, more specifically the construction of the upper assembly 36, the user can readily alternate between producing a sharply defined light spot having even brightness throughout and a less sharply defined light spot having intense brightness in an interior fading off toward peripheral outer edges.

The upper assembly 36 includes a cable mounting module 48 moveably mounted on a core module 50. Preferably, cable mounting and core modules 48 and 50 can be telescopically expanded and contracted. For example, compare FIGS. 2 and 3 and note arrow "A" denoting the direction of movement of cable mounting module 48 relative to core module 50. The result of displacing modules 48 and 50 is that the distance "A" between the end tip 22 of the fiber optic cable 20 and an adjacent convergent lens 52 can be intentionally altered. This adjustment affects the degree to which the optics in the headlamp 26 are defocused. For example, in the position illustrated in FIG. 2, the headlight can be used to produce a sharply defined light spot having even brightness throughout, and in the position illustrated in FIG. 3, the headlight can be used to produce a less sharply defined light spot having intense brightness in an interior fading off toward peripheral outer edges. While the distribution of light can be altered, the size, or diameter, of the light spot can remain unchanged, if desired.

The cable mounting module 48 includes a port 54 for releaseably engaging the end tip 22 of the fiber optic cable 20 and an opposite port 56 for telescopically mating with the core module 50. Preferably, port 54 includes a snap-ring 58 that engages a circumferential groove on the fiber optic cable 20 adjacent the end tip 22. This connection secures the end tip 22 in a fixed position relative to the cable mounting module 48. Preferably, port 56 includes an inner peripheral wall 60 that carries a secondary snap-ring, or detent spring, 62 used to engage the core module 50.

The core module 50 includes an end section 64 that is telescopically received within the cable mounting module 48. Section 64 has an outer peripheral surface 66 having two or more longitudinally-spaced, circumferentially-extending grooves, or recesses, 68 that can each be used to capture the detent spring 62 to lock the cable mounting and core modules, 48 and 50, together. The core module 50 can also include a stop pin (not shown) that extends from end section 64 and is engaged within a slot (not shown) in the wall 60 of module 48 to limit the range of movement of module 48 and end tip 22 relative to the optics contained within core module 50. The recesses 68 are located at positions that provide proper spacing between the end tip 22 and the optics in the headlamp to ensure that a desired distribution of light is produced within a projected light spot. By way of example, the detent 62 can be captured in the upper recess 68a as illustrated in FIG. 2 or in the lower recess 68b as shown in FIG. 3.

The core module 50 houses a pair of lenses, 52 and 72, and an iris 74. In the illustrated embodiments, lens 52, which is located adjacent to the end tip 22, is a convex lens having substantially symmetrical opposed convex surfaces, and lens 72 is a planoconvex lens. The iris 74 is located between lenses 52 and 72 and has an adjustable orifice which can be used to adjust the size of the light spot within a range of sizes. The planar surface 76 of lens 72 faces the iris 74 in upper assembly 26 illustrated in FIGS. 2 and 3. An iris ring 80 is carried by the core module 50 and provides an identification function when upper assembly 36 is provided in a kit with other upper assemblies. The iris ring 80 can be of a specific color that provides information to the user with respect to the spot sizes capable of being produced with the upper assembly.

In FIGS. 2 and 3, the upper assembly 36 is engageable with elbow assembly 44 which houses a mirror 82, spacer ring 84, an emitting, or exit, lens 86, and a lens ring 88. In elbow assembly 44, the spacer ring 84 is located between the mirror 82 and lens 86, and the lens 86 is a convex lens having opposed convex surfaces.

Figures 4, 5:
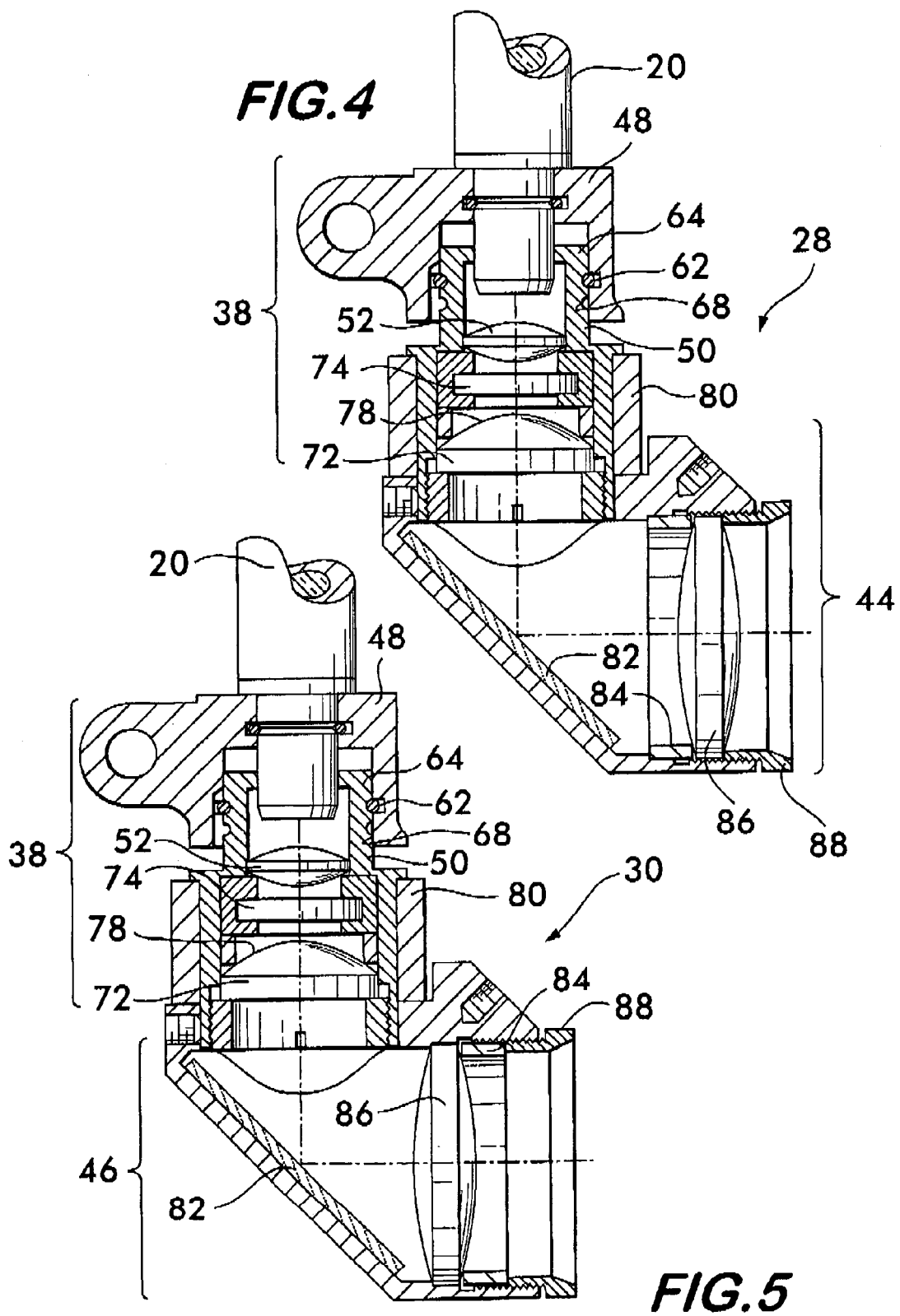
FIG. 4 is a cross-sectional view of a second embodiment of a headlamp assembly according to the present invention.
FIG. 5 is a cross-sectional view of a third embodiment of a headlamp assembly according to the present invention.

Turning to headlamp 28 in FIG. 4, it has similar components to that of headlamp 26 discussed above and provides a similar function. For example, elbow assembly 44 is used in both headlamps 26 and 28. Upper assembly 38 in FIG. 4 only differs from upper assembly 36 in that the convex surface 78 of lens 72 faces the iris in upper assembly 38. In addition, the color of the iris ring 80 on upper assembly 36 is different to permit ready visual differentiation between assemblies. The assembly of FIG. 4 can be utilized, for instance, to provide spots of small sizes, such as 105 mm in diameter. Thus, both upper assemblies 36 and 38 permit light distribution to be adjusted; however, each produces different ranges of spot sizes.

Turning to headlamp 30 in FIG. 5, it utilizes the same upper assembly 38 utilized by headlamp 28, discussed above, with an elbow assembly 46. Elbow assembly 46 includes a mirror 82, lens 86, spacer ring 84, and lens ring 86 in which the lens 86 is located between the mirror 82 and spacer ring 84. The assembly of FIG. 5 can be utilized, for instance, to provide spots of medium sizes, such as 115 mm in diameter.

Turning to headlamp 32 in FIG. 6, it has an upper assembly 40 that can be used when adjustment of the spacing "B" between the end tip 22 and convergent lens 52 is not desired. Thus, modules 48 and 50 are formed integrally and do not permit adjustment of light distribution style. The optics in upper assembly 40 are similar to those discussed with respect to the optics of upper assembly 38. Elbow assembly 44 is utilized with upper assembly 40, for instance, to provide spots about 105 mm in diameter on surfaces about sixteen inches from the headlamp.

Turning to headlamp 34 in FIG. 7, it has an upper assembly 42 that also does not permit adjustment of the spacing "B" between the end tip 22 and convergent lens 52. The optics in upper assembly 42 are similar to those discussed with respect to upper assembly 36. Elbow assembly 44 can be utilized with upper assembly 42, for instance, to provide spots about 140 mm in diameter on surfaces about sixteen inches from the headlamp.

As discussed above, preferably upper assemblies 36, 38, 40 and 42 are provided in a kit, or family, with elbow assemblies 44 and 46. Each upper assembly can be readily coupled to each elbow assembly. The user can determine the combination of upper assembly and elbow assembly to provide the desired light beam and spot characteristics. The upper and elbow assemblies are made of similar or the same components that are arranged differently, and each elbow component includes an iris ring 80 of a particular color, or like identification means, to distinguish one from the other present in the kit.

The present invention is also directed to a method of adjusting the light projected by a headlight system. The method includes securing a headband of a headlight system to the head of a user and attaching one end of a fiber optic cable to a light source and an opposite end tip to a headlamp mounted on the headband. Preferably, the headlamp has an upper assembly with a cable mounting module and a core module as discussed above. The cable mounting module has a port for releaseably engaging the end tip of the fiber optic cable, and the core module houses at least one convergent lens. The method includes the step of moving the cable mounting module relative to the core module to adjust a distance between the end tip of the fiber optic cable and the at least one lens in the core module. (See FIGS. 2-3.)

Preferably, the distance between the end tip of the fiber optic cable and the convergent lens is adjustable so that the headlamp can produce a sharply defined spot of light with substantially even brightness throughout. In addition, preferably this distance can be adjusted so that the headlamp can produce a spot of light with intense brightness in a center of the spot fading off towards peripheral edges of the spot.

Preferably, the headlight system is provided as a kit including multiple separate upper assemblies each releaseably engageable with an elbow assembly. The method can include the step of altering a size of the spot produced by the headlight system by using a different one of the upper assemblies with the elbow assembly. The kit can also include multiple separate elbow assemblies each having a mirror and an exit lens. The method can include the step of altering a size of the spot produced by the headlight system by using a different combination of upper and elbow assemblies. The assemblies can be made of similar or the same components, although arranged differently to provide different light beam and spot characteristics, such as spot size and light distribution.

While a preferred headlight and method have been described in detail, various modifications, alterations, and changes may be made without departing from the spirit and scope of the headlight and method according to the present invention as defined in the appended claims.

The invention claimed is:

1. A headlight system, comprising a headband, a headlamp mounted on said headband, a light source, and a fiber optic cable having one end connected to said light source and an opposite end tip connected to said headlamp, said headlamp including:

an upper assembly having a cable mounting module and a core module, said cable mounting module having a port for releaseably engaging said end tip of said fiber optic cable and said core module housing at least one lens, said cable mounting module being telescopically engageable with said core module and being moveable and lockable at fixed positions relative to said core module without disassembly of said headlamp to adjust a distance between said end tip of said fiber optic cable and said lens in said core module; and an elbow assembly connected to said core module of said upper assembly and having a mirror and an exit lens;

whereby, adjusting said distance between said end tip of said fiber optic cable and said lens in said core module permits said headlamp to produce a sharply defined spot of light with substantially even brightness throughout and a less sharply defined spot of light with intense brightness in a center of the spot fading off towards peripheral edges of the spot.

2. A headlight system according to claim 1, wherein one of said cable mounting and core modules has an outer peripheral surface with multiple longitudinally-spaced recesses and the other has an inner peripheral surface telescopically receivable over said outer peripheral surface, said inner peripheral surface including a detent that cooperates with said recesses for locking said cable mounting module at said fixed positions relative to said core module.

3. A headlight system according to claim 2, wherein said at least one lens in said core module includes a convex lens and a planoconvex lens.

4. A headlight system according to claim 3, wherein said convex lens has substantially symmetrical opposed convex surfaces, and wherein an iris diaphragm is mounted within said core module between said convex and planoconvex lenses.

5. A headlamp kit for a headlight system, comprising:
- a plurality of upper assemblies each housing a convex lens and a planoconvex lens and having a port for releaseably engaging an end tip of a fiber optic cable; and
- at least one elbow assembly housing a mirror and an exit lens and being releaseably engageable with each of said upper assemblies;
- each of said upper assemblies having a different arrangement of said convex and planoconvex lenses and thereby said upper assemblies permit illuminated light spots of different sizes or types to be produced.

6. A kit according to claim 5, wherein said convex lens of each upper assembly has substantially symmetrical opposed convex surfaces.

7. A kit according to claim 6, wherein each of said upper assemblies has an iris diaphragm located between said convex and planoconvex lenses.

8. A kit according to claim 7, wherein a planar surface of said planoconvex lens faces said iris diaphragm in one of said upper assemblies, and wherein a convex surface of said planoconvex lens faces said iris diaphragm in another of said upper assemblies.

9. A kit according to claim 8, wherein each of said upper assemblies includes a unique identification element.

10. A kit according to claim 9, wherein said identification elements are outer iris rings of different colors located on said upper assemblies.

11. A kit according to claim 5, wherein said kit includes at least a pair of said elbow assemblies, wherein each of said elbow assemblies houses a mirror, a lens spacer ring, and an exit lens, and wherein said spacer ring is located between said mirror and said exit lens in one of said elbow assemblies and said exit lens is located between said mirror and said spacer ring in the other of said elbow assemblies.

12. A kit according to claim 5, wherein at least one of said upper assemblies comprises a cable mounting module and a core module, said cable mounting module having a port for releaseably engaging an end tip of a fiber optic cable and said core module housing said convex and planoconvex lenses, said cable mounting module being moveable relative to said core module to adjust a distance between the end tip of the fiber optic cable and said lenses in said core module.

13. A kit according to claim 12, wherein said cable mounting module and core module are telescopically engageable.

14. A kit according to claim 13, wherein one of said cable mounting and core modules has an outer peripheral surface with multiple longitudinally-spaced recesses and the other has an inner peripheral surface telescopically receivable over said outer peripheral surface, said inner peripheral surface including a detent that cooperates with said recesses for locking said cable mounting module at a fixed position relative to said core module.

15. A method of adjusting the light projected by a headlamp of a headlight system, comprising the steps of:
- securing a headband of a headlight system to the head of a user;
- attaching one end of a fiber optic cable to a light source and an opposite end tip to a headlamp mounted on the headband, the headlamp having an upper assembly with a cable mounting module and a core module, the cable mounting module having a port for releaseably engaging the end tip of said fiber optic cable and the core module housing at least one lens; and
- moving the cable mounting module relative to the core module and locking the cable mounting module at one of a plurality of fixed positions relative to the core module without disassembly of the headlamp to adjust a distance between the end tip of the fiber optic cable and the at least one lens in the core module.

16. A method according to claim 15, wherein the distance between the end tip of the fiber optic cable and the at least one lens is adjusted so that the headlamp produces a sharply defined spot of light with substantially even brightness throughout.

17. A method according to claim 16, wherein the distance between the end tip of the fiber optic cable and the at least one lens is adjusted so that the headlamp produces a spot of light with intense brightness in a center of the spot fading off towards peripheral edges of the spot.

18. A method according to claim 17, further comprising the steps of:
- providing a kit including multiple ones of said upper assembly each releaseably engageable with an elbow assembly having a mirror and an exit lens, each upper assembly having a different arrangement of lenses; and
- altering a size of the spot produced by the headlight system by using a different upper assembly with said elbow assembly.

19. A method according to claim 18, further comprising the steps of:
- providing multiple of said elbow assemblies having different spacing between the mirror and the exit lens; and
- altering a size of the spot produced by the headlight system by using a different combination of upper assembly and elbow assembly.

* * * * *